(12) United States Patent
Zheng

(10) Patent No.: US 11,317,902 B2
(45) Date of Patent: May 3, 2022

(54) SST RETRACTOR WITH RADIOLUCENT FEATURE

(71) Applicant: DEPUY SYNTHES PRODUCTS, INC., Raynham, MA (US)

(72) Inventor: Guangliang Zheng, Suzhou (CN)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 94 days.

(21) Appl. No.: 16/622,810

(22) PCT Filed: Jun. 15, 2017

(86) PCT No.: PCT/CN2017/088368
§ 371 (c)(1),
(2) Date: Dec. 13, 2019

(87) PCT Pub. No.: WO2018/227446
PCT Pub. Date: Dec. 20, 2018

(65) Prior Publication Data
US 2021/0145428 A1     May 20, 2021

(51) Int. Cl.
*A61B 17/02* (2006.01)
*A61B 17/00* (2006.01)

(52) U.S. Cl.
CPC .. *A61B 17/0206* (2013.01); *A61B 2017/0092* (2013.01)

(58) Field of Classification Search
CPC ............ A61B 17/0206; A61B 17/0092; A61B 2017/0268; A61B 2017/0225; A61C 17/10; A61M 16/0495; B63H 16/04
See application file for complete search history.

(56) References Cited

U.S. PATENT DOCUMENTS

| 1,100,312 A | * | 6/1914 | Leino | ..................... F16G 11/06 403/394 |
| 8,100,828 B2 | | 1/2012 | Frey et al. | |

(Continued)

FOREIGN PATENT DOCUMENTS

| JP | 2006-507099 B2 | 3/2006 |
| JP | 2007-514501 B2 | 6/2007 |

(Continued)

OTHER PUBLICATIONS

International Search Report and Written Opinion, International Application No. PCT/CN2017/088368, dated Mar. 15, 2018, 15 pages.

(Continued)

*Primary Examiner* — Julianna N Harvey
*Assistant Examiner* — Holly Joanna Lane
(74) *Attorney, Agent, or Firm* — Raymond N. Scott, Jr

(57) ABSTRACT

A radiolucent tissue retraction device (100), comprises a handle (106) extending along a handle axis ($L_h$) and a first paddle (102) coupled to a first end (103) of the handle (106), the first paddle (102) including a first portion (110) extending parallel to and offset from the handle (106) and a second portion (116) connecting the first portion (110) to the handle (106), the first portion (110) having at least one radiolucent feature extending into a surface thereof, wherein the first portion (110) is curved along a longitudinal axis ($L_1$) thereof.

21 Claims, 4 Drawing Sheets

(56) References Cited

U.S. PATENT DOCUMENTS

| | | | |
|---|---|---|---|
| 8,636,654 B2* | 1/2014 | Protopsaltis | A61B 1/32 600/201 |
| 10,093,404 B1* | 10/2018 | Mariansky | B63H 16/08 |
| 10,398,299 B2 | 9/2019 | Hawk et al. | |
| 10,464,102 B2 | 11/2019 | Akiyama et al. | |
| 10,869,657 B2 | 12/2020 | Raymond et al. | |
| 10,966,702 B1* | 4/2021 | Swift | A61B 90/30 |
| 2002/0095139 A1* | 7/2002 | Keogh | A61B 17/0206 606/1 |
| 2004/0015173 A1 | 1/2004 | Irving | |
| 2005/0085723 A1 | 4/2005 | Huebner | |
| 2005/0107671 A1* | 5/2005 | McKinley | A61B 17/025 600/235 |
| 2006/0052671 A1* | 3/2006 | McCarthy | A61B 17/0206 600/232 |
| 2007/0038033 A1 | 3/2007 | Jones et al. | |
| 2008/0090207 A1 | 4/2008 | Rubbert | |
| 2008/0146885 A1 | 6/2008 | Protopsaltis | |
| 2011/0093075 A1* | 4/2011 | Duplessis | A61F 2/44 623/17.16 |
| 2012/0265021 A1* | 10/2012 | Nottmeier | A61B 17/0206 600/219 |
| 2012/0316430 A1* | 12/2012 | Aldag | A61B 17/02 600/424 |
| 2014/0265789 A1 | 9/2014 | Metzler | |
| 2014/0275797 A1 | 9/2014 | Ibrahim et al. | |
| 2015/0196289 A1 | 7/2015 | Ryshkus et al. | |
| 2015/0313456 A1 | 11/2015 | Hawkins et al. | |
| 2016/0030128 A1* | 2/2016 | Duggal | A61B 17/02 600/246 |
| 2017/0311941 A1* | 11/2017 | Daavettila | A61B 17/0206 |
| 2020/0345339 A1* | 11/2020 | Radl | A61B 17/0206 |

FOREIGN PATENT DOCUMENTS

| | | |
|---|---|---|
| JP | 2009-254752 A | 5/2011 |
| JP | 2011-115408 B2 | 6/2011 |
| JP | 2014-534868 A | 12/2014 |
| JP | 2016-521997 B2 | 7/2016 |

OTHER PUBLICATIONS

JP2019-569458—Corresponding JP Exam Report dated Mar. 23, 2021.

English Translation—JP2011115408A_Abstract Dated Jun. 16, 2011.

* cited by examiner

SST RETRACTOR WITH RADIOLUCENT FEATURE

CROSS REFERENCE TO RELATED APPLICATION

This application is a National Stage Application filed Under 35 U.S.C. § 371 of International Application No. PCT/CN2017/088368 filed Jun. 15, 2017, published Dec. 20, 2018 as International Publication No. WO2018/227446 A1 which is hereby incorporated by reference in its entirely.

BACKGROUND

Retractors are often used for permitting access to a bone structure intended for osteotomy procedures while at the same time providing protection for various soft tissue members. The development of surgical retractors and techniques that minimize the size of incisions has yielded major improvements in recovery time and post-operative pain because by reducing the required dissection of tissue. However, visualization of the retractor may be difficult, particularly when the procedure occurs at a location deep within the body of the patient. In orthopaedic surgery, it is extremely important that surgical tools such as retractors have good reliability (i.e., strength), biocompatibility and radiolucency. Currently, retractors for use in osteotomies, for example, have generally been designed using polyether ether ketone (PEEK), aluminum or Stainless Steel (SST). However, none of these materials has the ideal combination of characteristics for use in an osteotomy. The reliability of retractors composed of PEEK has often been poor while manufacturing cost is high. Aluminum retractors may be toxic and have also displayed poor reliability, while the radiolucency of retractors composed of SST is low.

SUMMARY

The described embodiments of the invention are directed to a radiolucent tissue retraction device. The device may generally be described as comprising a handle extending along a handle axis and a first paddle coupled to a first end of the handle, the first paddle portion including a first portion extending parallel to and offset from the handle and a second portion connecting the first portion to the handle, the first portion having at least one radiolucent feature extending into a surface thereof, wherein the first portion is curved along a longitudinal axis thereof.

BRIEF DESCRIPTION

DETAILED DESCRIPTION

Figure 1:
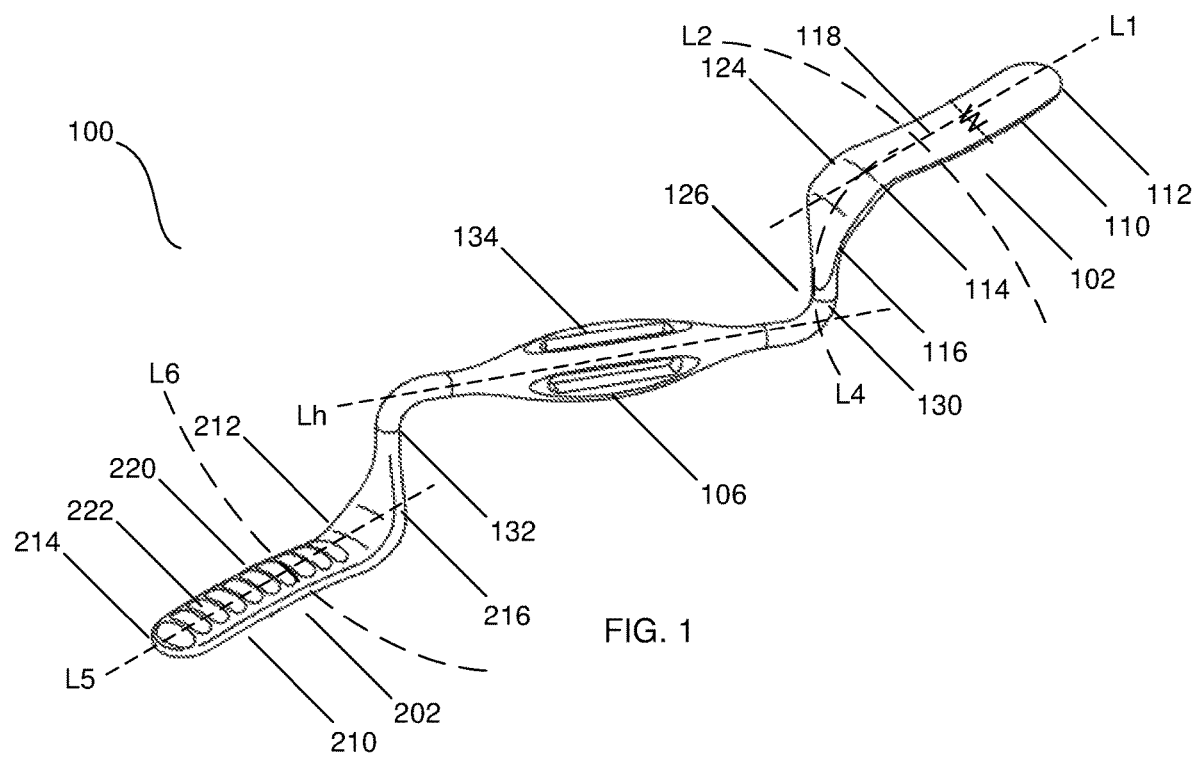
FIG. 1 shows a perspective view of a retractor according to an exemplary embodiment of the present disclosure.

The present disclosure may be further understood with reference to the following description and the appended drawings, wherein like elements are referred to with the same reference numerals. The present disclosure is directed to orthopedic medical devices and, in particular, relate to surgical retractors including a radiolucent feature. Those skilled in the art will appreciate that the principles of the invention apply to any handheld medical device that is inserted into a patient during a surgical procedure. It should be noted that the terms "proximal" and "distal" as used herein are intended to refer to a direction toward (proximal) and away from (distal) a user of the device.

FIGS. 1-5 show a Stainless Steel retractor 100 positioned during a surgical procedure to move or retain tissue along an approach to an operative site within the patient's body. For example, in osteotomy surgery, the retractor 100 may be used to protect anatomical structures. Although the device may be used without limitation, the description and examples herein refer to structures dorsal to the posterior tibial surface. Those skilled in the art will recognize that the device may be used in other areas of the anatomy where a retraction is desired.

Figure 2:
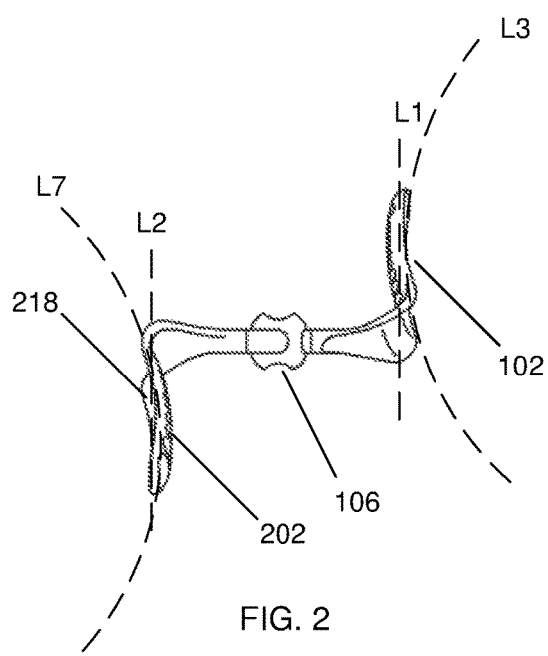
FIG. 2 shows a front plan view of the retractor of FIG. 1 rotated 90 degrees.
Figure 5:
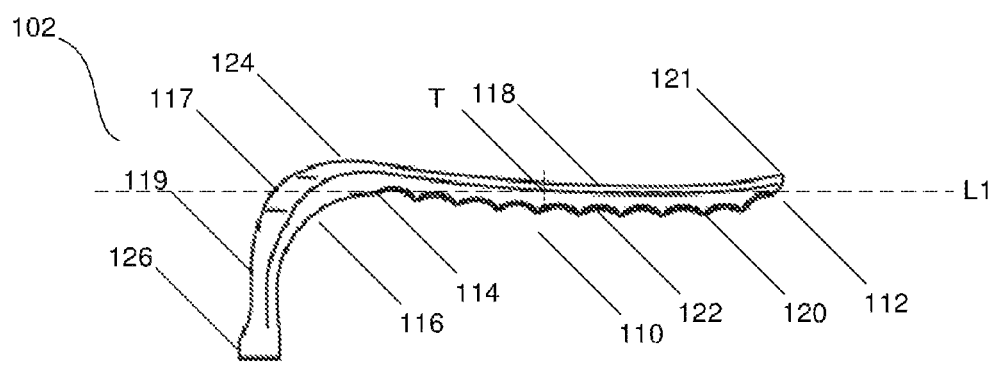
FIG. 5 shows a side plan view of the paddle portion of the retractor of FIG. 1.

The retractor 100 includes two paddles 102, 202 and a handle 106. The first paddle 102 is coupled to a proximal end 130 of the handle 106 while the second paddle 202 is coupled to a distal end 132 of the handle 106. The first paddle 102 includes a first part 110 extending from a proximal end 112 to a distal end 114 and a second part 116 extending from the first part distal end 114 and including a substantially 90 degree bend. The first part 110 according this embodiment is an elongated member with a rounded proximal end 112 and a length along a longitudinal axis $L_1$. The first part 110 includes a bone-contacting first surface 118, and an opposing second surface 120 and has a width W (i.e., an extent in a direction perpendicular to the axis $L_1$) that is, in this embodiment, shorter than its length and substantially uniform along the length of the first part 110. In this embodiment, the first part 110 is curved about a first curvature axis $L_2$ perpendicular to the central longitudinal axis, $L_1$, as shown in FIG. 2, such that the first surface 118 is concave while the second surface 120 opposite the first surface 118 is convex. In this exemplary embodiment, the first part 110 is also curved about a curved axis $L_3$ (e.g., parallel to and radially within the curve of the first surface 118 about $L_2$) as shown in FIG. 2 such that the bone-contacting first surface 118 is concave and the second surface 120 is convex with respect to $L_3$. This curvature along the length of first part 110 allows the retractor to be easily inserted between the bone and tissue and the shape of the first part 110 is selected so that the bone-contacting first surface 118 fits a shape of a bone against which it is to be positioned. The first part 110 has a thickness T which, in this embodiment is generally uniform along its length and width (except for the tip 121 as described below) and which may be, for example, approximately 2 mm. At the proximal end 112, a proximal portion of the second surface 120 of this embodiment curves toward the first surface 118 such that the thickness T decreases to, for example, 1 mm to form a tip 121, as shown in FIG. 5. This tip 121 allows the first part 110 to be inserted more easily between the tissue and the bone without undue trauma to either.

Figure 4:
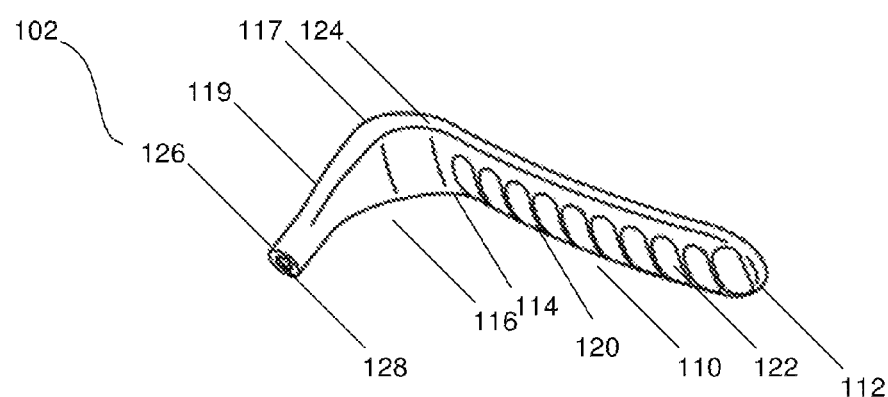
FIG. 4 shows a perspective view of the paddle portion of the retractor of FIG. 1, according to an exemplary embodiment of the present disclosure.

The first part 110 includes a plurality of radiolucent features including a plurality of slots and/or grooves 122 which, in this exemplary embodiment, extend perpendicular to the longitudinal axis $L_1$ separated from one another along the length of the first portion 110. The grooves 122 are formed in the second surface 120. As would be understood by those skilled in the art, the radiolucency of the grooves 122 depends on the density of the Stainless Steel and the attenuation of length of the structure (i.e., thickness of the material). In an exemplary embodiment using Type 1.4542 Stainless Steel, the thickness of the first part 110 at the greatest depth of the grooves 122 (i.e., the minimum thickness of the material of the first part 110) is approximately 0.3 mm. The depth of these grooves 122 enhances the radiolucency of the first part 110. However, if this minimum thickness were applied uniformly over the surface of the first part 110 may be too thin to withstand the stresses applied during surgery. Thus, the grooves 122 are concave leaving an increased thickness of material toward the lateral surfaces of the first part 110. The thicker lateral sides of the first part 110 provide the stability required to withstand the stresses applied during use enhancing the reliability of the retractor 100 which increasing the radiolucency of the device. The grooves 122 are, in this embodiment, generally oval as illustrated in FIG. 4. However, it will be understood that the grooves 122 may take any shape or form so long as at their greatest depth, the thickness of the first part 110 is approximately 0.3 mm while the thickness of the lateral portions of the first part 110 is at least 2 mm. The exemplary embodiment of FIG. 4 provides ten grooves 122 distributed along the length of the first part 110. However it is noted that any number of grooves 122 may be used. The grooves 122 may be distributed along the entire length of the first part 110 or may only be distributed only along a portion of its length. For example, the grooves 122 may be distributed along a proximal portion of the first part 110. In another example, only a medial portion of the first part 110 may include grooves 122.

Figure 6:
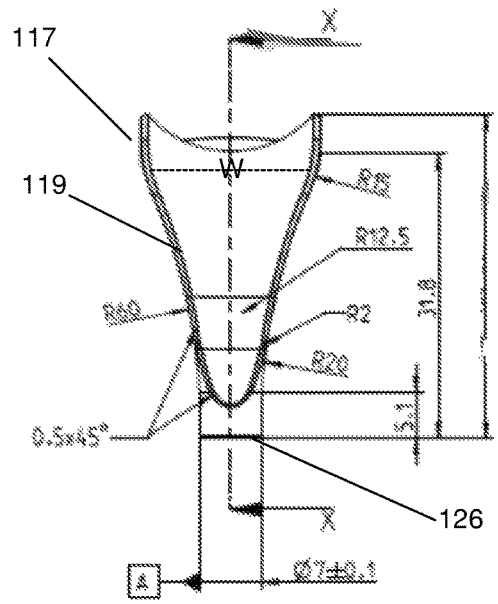
FIG. 6 shows a perspective side view of the second portion of the paddle portion of the retractor of FIG. 1.

The second part 116 extends from a proximal end 124 connected to the distal end 114 of first part 110 to a distal end 126 connected to the handle 106. In this embodiment, the second part 116 includes a curved portion 117 having an approximately 90-degree bend and a tapered portion 119. The curved portion 117 curves from a plane including the first part 110 to a plane perpendicular to the first part 110. In this exemplary embodiment, the width of the curved portion 117 is approximately equal to the width of the first part 110. However, the width of the tapered portion 119 decreases from a proximal end connected to a distal end of the curved portion 117 to the distal end 126 of second part 116 to form a substantially U or V-shape. For example, in the embodiment of FIG. 6, the distance between the lateral sides of the tapered portion 119 decreases toward the distal end 126 so that the width of the distal end 126 is smaller than the width of the curved portion 117. In an exemplary embodiment, the width of the distal end 126 is, for example, 7 mm. The V-shape of the tapered portion 119 allows the user to cut through a posterior side of a bone without being blocked by the second part 116. The second part 116 is curved about a curved axis $L_4$ (e.g., parallel to and radially within the curve of the first surface 118) as shown in FIG. 2 such that the first surface 118 is concave and the second surface 120 is convex with respect to $L_4$ (except for the distal portion as described below). As can be seen in FIG. 6, the curvature of second part 116 ends just proximal of the distal end 126 so that, in this embodiment, the distal end 126 of the second part 116 is substantially cylindrical. This provides a more stable connection between the first paddle 102 and the handle 106. In this embodiment, the distal end 126 includes a coupling means 128, as can be seen in FIG. 4, for coupling the first paddle 102 to the handle 106. In another exemplary embodiment, the distal end 126 may be welded to the handle 106. In a further embodiment, the first paddle 102 may be integrally formed with the handle 106.

The handle 106 extends from a proximal end 130 coupled to the distal end 126 of the second part 116 to a distal end 132 coupled to a proximal end 212 of the second paddle 202 along a longitudinal axis $L_h$. In this embodiment, the handle 106 may be substantially cylindrical about a medial portion with tapering proximal and distal ends. It will be understood that the handle 106 may take any shape providing a stable connection between the first and second paddles 102, 202 as well as a suitable surface for gripping. The handle 106 may include a plurality of slots 134 distributed radially about the outer surface of the handle 106 for enhanced gripability when in use. The handle 106 may be formed of Stainless Steel or any other suitable biocompatible material.

Figure 3:
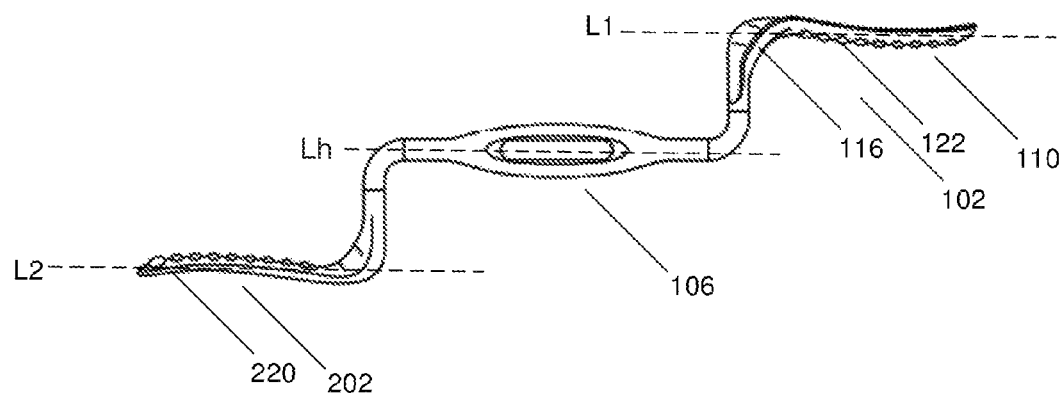
FIG. 3 shows a side plan view of the retractor of FIG. 1.

The second paddle 202 in this embodiment is configured substantially similarly to the first paddle 102. Specifically, the second paddle 202 includes a first part 210 extending from a proximal end 212 to a distal end 214 and a second part 216 extending from the first part proximal end 212 and including a substantially 90 degree bend. The first part 210 according to this embodiment is an elongated member with a rounded distal end 214 and a length along a longitudinal axis $L_5$. The first part 210 includes a bone contacting first surface 218 and an opposing second surface 220 and has a width W (i.e., an extent in a direction perpendicular to the axis $L_5$) that is, in this embodiment, shorter than its length and substantially uniform along the length of the first part 210. In this embodiment, the first part 210 is curved about a first curvature axis $L_6$ perpendicular to the central longitudinal axis, $L_5$, as shown in FIG. 2, such that the first surface 218 is concave while the second surface 220 opposite the first surface 118 is convex. Similar to first part 110, in this exemplary embodiment, the first part 210 is also curved about a curved axis $L_7$ (e.g., parallel to and radially within the curve of the first surface 218 about $L_5$) as shown in FIG. 2 such that the bone-contacting first surface 218 is concave and the second surface 220 is convex with respect to L7. The first part 210 also has a thickness T which is generally uniform along its length and width (except for tip 221) and which may be, for example, approximately 2 mm. At the distal end 214, a proximal portion of the second surface 220 of this embodiment curves toward the first surface 218 such that the thickness T decreases to, for example 1 mm to form a tip 221, as shown in FIG. 3.

As with first portion 110, the first portion 210 includes a plurality of radiolucent features including a plurality of grooves 222 which, in this exemplary embodiment, extend perpendicular to the longitudinal axis $L_5$ and are separated from one another along the length of the first portion 210. The grooves 222 are formed in the same manner as grooves 122. Namely, in an exemplary embodiment using Type 1.4542 Stainless Steel, the thickness of the first part 210 at the greatest depth of grooves 222 (i.e., the minimum thickness of the material of the first part 210) is approximately 0.3 mm. The grooves 22 are also concave leaving an increased thickness of material toward the lateral surface of the first part 210. In this embodiment, the grooves 22 are generally oval however, it will be understood that the grooves 222 may take any shape or form so long as at their greatest depth, the thickness of the paddle 202 is approximately 0.3 mm while the thickness of the lateral portions of the first part 210 is at least 2 mm.

The second part 216 extends from a proximal end 224 connected to the distal end 132 of the handle to a distal end 226 connected to the proximal end 212 of the first part 210.

In this embodiment, the second part 216 includes a curved portion 217 having an approximately 90-degree bend and a tapered portion 219. The curved portion 217 curves from a plane including the first part 210 to a plane perpendicular to the first part 210. In this exemplary embodiment, the width of the curved portion 217 is approximately equal to the width of the first part 210. However, the width of the tapered portion 219 decreases from a distal end connected to a proximal end 212 of the first part 210 to a distal end 132 of the handle 106 to form a substantially U or V-shape. For example, in the embodiment of FIG. 6, the distance between the lateral sides of the tapered portion 219 decreases toward the proximal end 224 so that the width of the proximal end of the tapered portion 219 is smaller than the width of the curved portion 217. In an exemplary embodiment, the width of the proximal end 224 is, for example, 7 mm. The second part 216 is curved about a curved axis $L_8$ (e.g., parallel to and radially within the curve of the first surface 118) as shown in FIG. 2 such that the first surface 218 is concave and the second surface 220 is convex with respect to $L_8$ (except for the proximal portion as described below). Similar to the second part 116, the curvature of second part 216 ends just distal of the proximal end 224 so that, in this embodiment, the proximal end 224 of the second part 216 is substantially cylindrical. This provides a more stable connection between the second paddle 202 and the handle 106. In this embodiment, the proximal end 224 includes a coupling means for coupling the second paddle 202 to the handle 106. In another exemplary embodiment, the proximal end 224 may be welded to the handle 106. In a further embodiment, the second paddle 202 may be integrally formed with the handle 106.

Figure 7:
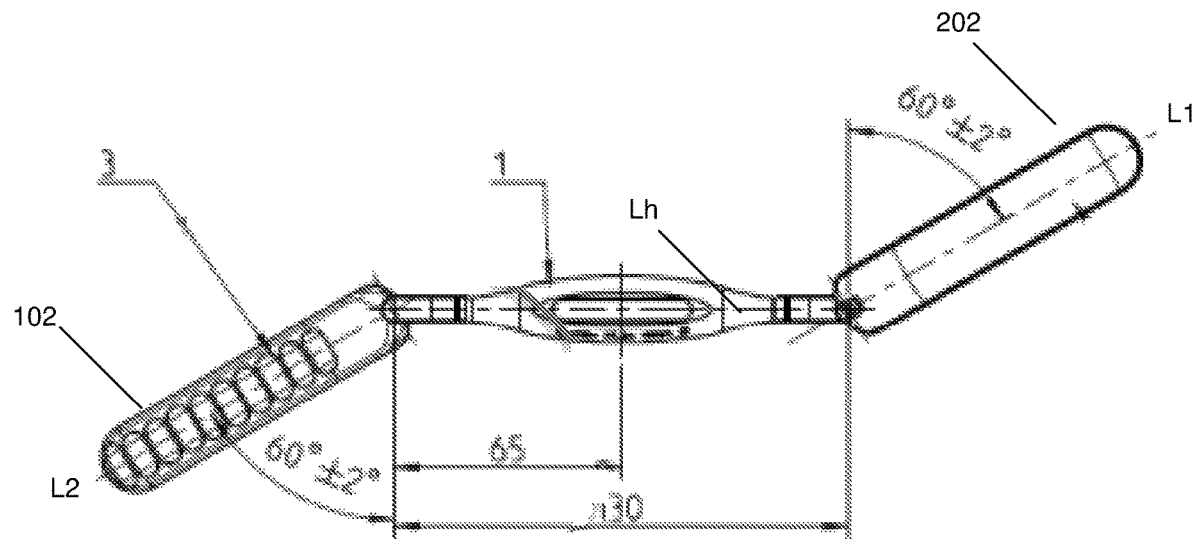
FIG. 7 shows a top view of the retractor of FIG. 1.

The first and second paddles 102, 202 are coupled to the handle 106 so that the tapered portions 119, 219 extend perpendicular to a plane including the longitudinal axis of the handle. The tapered portion 119 extends perpendicular to the longitudinal axis $L_h$ of the handle 106 in a first direction while the tapered portion 219 extends perpendicular to the longitudinal axis $L_h$ of the handle 106 in an opposing direction, as can be seen in FIG. 3. Thus, the first paddle first part 110 is positioned in a plane substantially parallel to a plane including the handle 106 and the second paddle first part 210, as illustrated in FIG. 3. Specifically, the first part 110 of the first paddle 102 is substantially parallel to a plane including the longitudinal axis $L_h$ of the handle 106 in a direction opposite the first part 210 of the second paddle 202, as shown in FIG. 4. More specifically, the first and second paddle portions 102, 202 are coupled to the handle 106 so that the second surface 120 of the first paddle 102 and the second surface 220 of the second paddle 202 face a plane extending through the handle 106. As can be seen in FIG. 7, the first and second paddles 102, 202 are coupled to the handle so that the longitudinal axes $L_1$ and $L_5$ are laterally rotated approximately 60+/−2 degrees from the longitudinal axis $L_h$ of the handle 106. In this embodiment, the first and second paddles 102, 202 are rotated toward opposing lateral sides of the handle, as shown in FIG. 7. This rotation ensures that the paddles 102, 202 do not block the surgeon's access to the bone and surrounding tissue during surgery.

The material of the retractor 100 of this embodiment is stainless steel which provides a high level of strength and reliability as well as improved radiolucent qualities, especially when combined with the thinner grooved portions 122, 222 disclose above. In an exemplary embodiment, the retractor is formed of Type 1.4542 Stainless Steel. In other embodiments, the retractor may be formed of 1.4301, 1.4021, 1.4310 Stainless Steels or any other suitable Stainless Steel variation. Stainless steel also shows high levels of biocompatibility to prevent from any toxicity when in the human body. Various techniques may be used to manufacture the device at a relatively low cost. For example, the retractor may be manufactured by machining, welding, finish, or heat treating.

Figure 8:
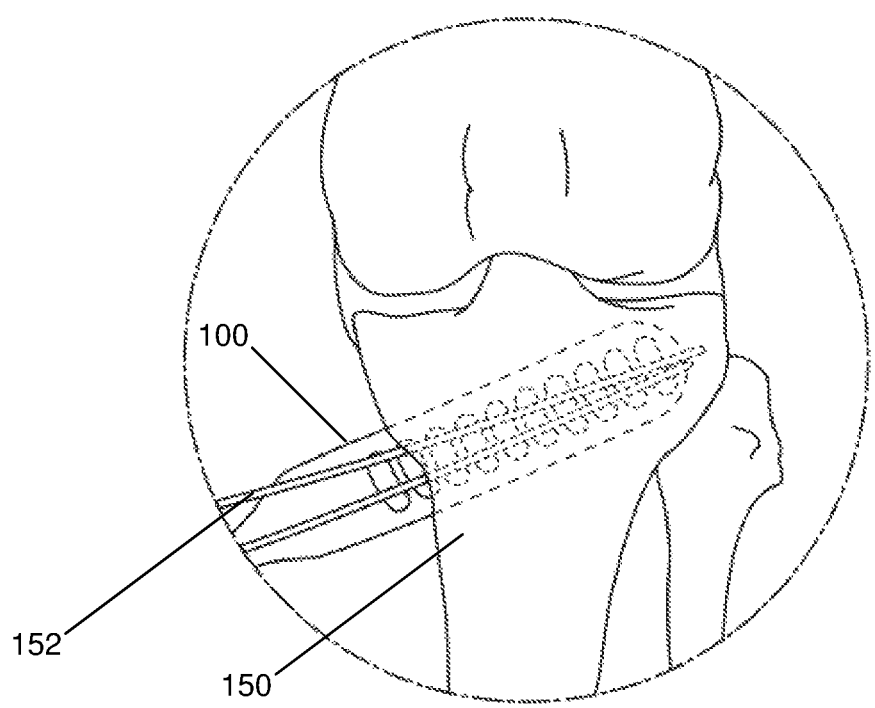
FIG. 8 shows a perspective view of the retractor of FIG. 1 when in an operative position.

Referring now to FIG. 8, one example of a method for imaging the retractor 100 and surgical site in the patient will be described. An incision is made in skin adjacent the location of a patient's anatomy to be accessed. For example, in knee surgery, the incision may be made at the medial side of the tibia, approximately one centimeter below the joint line and extending to the pes anserinus tendons to provide access to the posterior tibial surface. The retractor 100 is then inserted through the incision to a target position near behind the tibia 150 (such as dorsal to the posterior tibial surface between the tibia and anatomical structures to be protected) to expose the posterior ridge of the tibia. An imaging system (not shown), such as an X-ray, CT scan, radiographic or other imaging system may be used to provide to the surgeon images of the surgical approach and operative site through the tissue of the patient and through the radiolucent portion of the retractor 100. Furthermore, the location and orientation of instruments 152 and implants used at the operative site may be visualized using with the imaging system (not shown) through the radiolucent portion of the retractor 100 and the tissue of the patient. Once the procedure has been performed, the retractor 100 is removed from the target position and the incision is closed.

It will be appreciated by those skilled in the art that changes may be made to the embodiments described above without departing from the inventive concept thereof. It should further be appreciated that structural features and methods associated with one of the embodiments can be incorporated into other embodiments. It is understood, therefore, that this invention is not limited to the particular embodiments disclosed, but rather modifications are also covered within the scope of the present invention as defined by the appended claims.

What is claimed is:

1. A radiolucent tissue retraction device, comprising:
a handle extending along a longitudinal handle axis, the handle having a first end and a second end opposite the first end;
a first paddle coupled to the first end of the handle, the first paddle including a first portion extending parallel to and offset from the handle and a second portion connecting the first portion of the first paddle to the handle, the first portion of the first paddle having at least one radiolucent feature extending into a surface thereof, wherein the first portion of the first paddle is curved along a longitudinal axis thereof and has a bone contacting surface configured to fit against a shape of a bone, the first portion of the first paddle disposed generally along a first plane; and
a second paddle coupled to the second end of the handle, the second paddle including a first portion extending parallel to and offset from the handle and a second portion connecting the first portion of the second paddle to the handle, the first portion of the second paddle disposed generally along a second plane;
wherein the handle is disposed between the first plane and the second plane; and
wherein the longitudinal axes of the first portion of the first paddle and the first portion of the second paddle are angled with respect to the longitudinal handle axis.

2. The device of claim 1, wherein the second paddle has at least one radiolucent groove extending into a surface thereof.

3. The device of claim 1, wherein the at least one radiolucent feature is a groove.

4. The device of claim 3, wherein the first and second paddles are formed of 1.4542 Stainless Steel.

5. The device of claim 1, wherein the longitudinal axes of the first portion of the first paddle and the first portion of the second paddle are angled approximately 60+/−2 degrees with respect to the longitudinal handle axis.

6. The device of claim 1, wherein the first portion of the second paddle is curved along a longitudinal axis thereof and has a bone contacting surface configured to fit against a shape of a bone.

7. The device of claim 1, wherein the first portion of the first paddle is disposed approximately 90-degrees to the second portion of the first paddle.

8. The device of claim 1, wherein the thickness of the first paddle at the radiolucent feature is approximately 0.3 mm.

9. A tissue retraction device for surgery in a patient, comprising:
   a retractor comprising a first elongated paddle extending between a proximal end and a distal end, wherein the distal end of the first elongated paddle is positionable in the patient, the first elongated paddle including at least one radiolucent feature extending between the distal and proximal ends and between opposing lateral sides of the first elongated paddle, the first elongated paddle being formed of stainless steel, the first elongated paddle configured to fit against a posterior tibial surface,
   the retractor further comprising a second elongated paddle extending between a proximal end and a distal end, wherein the proximal end of the second elongated paddle is positionable in the patient; and
   a handle extending from a proximal end to a distal end and having a longitudinal axis, the distal end of the handle coupled to the proximal end of the first elongated paddle, the proximal end of the handle coupled to the distal end of the second elongated paddle; and
   wherein a longitudinal axis of the first elongated paddle and a longitudinal axis of the second elongated paddle are angled with respect to the longitudinal axis of the handle; and
   wherein the longitudinal axis of the handle is disposed in between the longitudinal axis of the first elongated paddle and the longitudinal axis of the second elongated paddle.

10. The device of claim 9, wherein the at least one radiolucent feature is a groove.

11. The device of claim 9, wherein the first and second elongated paddles are formed of 1.4542 Stainless Steel.

12. The device of claim 11, wherein the longitudinal axes of the first and second elongated paddles are angled approximately 60+/−2 degrees with respect to the longitudinal axis of the handle.

13. The device of claim 9, wherein the longitudinal axis of each the first and second elongated paddles is angled with respect to the longitudinal axis of the handle.

14. The device of claim 9, wherein a free end of each of the first and second elongated paddles includes a first bone-contacting surface and a second opposing surface, the second opposing surface curving toward the first surface at a free end to form a tip at the free end.

15. The device of claim 9, wherein the first elongated paddle tapers at a distal portion thereof.

16. The device of claim 9, wherein the thickness of the first elongated paddle at the radiolucent feature is approximately 0.3 mm.

17. A method of tissue retraction without visualization impairment, comprising:
   inserting a retractor to an operative site within a body, the retractor positioned to protect a target anatomical structure, the retractor comprising:
   a handle lying in a first plane; and
   a first paddle coupled to a first end of the handle, the first paddle including a first portion and a second portion, the first portion lying in a second plane generally parallel to the first plane and having at least one radiolucent feature extending into a surface thereof, the second portion including a bend, wherein the first portion of the first paddle is curved along a longitudinal axis thereof;
   a second paddle coupled to a second end of the handle, the second paddle including a first portion and a second portion, the first portion of the second paddle lying in a third plane generally parallel to the first plane;
   wherein the first plane is disposed between the second plane and the third plane; and
   wherein a longitudinal axis of the first portion of the first paddle and a longitudinal axis of the first portion of the second paddle are angled with respect to a longitudinal axis of the handle; and
   determining the location and orientation of instruments or anatomical features within the operative site through the radiolucent feature of the first portion of the first paddle using an imaging system.

18. The method of claim 17, further comprising making an incision in skin adjacent the location of the operative site to be accessed.

19. The method of claim 17, wherein the at least one radiolucent feature is a groove, the thickness of the first paddle at the radiolucent feature is approximately 0.3 mm.

20. A radiolucent tissue retraction device, comprising:
   a handle extending along a handle axis;
   a first paddle coupled to a first end of the handle, the first paddle including a first part extending along a first paddle axis parallel to and laterally offset from the handle axis, and a second part connected to the first part, the second part of the first paddle connecting the first paddle to the handle and extending transverse to the handle and first paddle axis, the first part of the first paddle including at least one radiolucent feature formed in a surface thereof, wherein the first part of the first paddle is curved about a first curvature axis transverse to the first paddle axis; and
   a second paddle coupled to a second end of the handle, the second paddle including a first part extending along a second paddle axis parallel to and laterally offset from the handle axis, and a second part connected to the first part of the second paddle, the second part of the second paddle connecting the second paddle to the handle and extending transverse to the handle and second paddle axes, wherein the second part is curved about a second curvature axis transverse to the first paddle axis
   wherein the first part of the first paddle is angled approximately 60+/−2 degrees with respect to the longitudinal axis of the handle and the first part of the second paddle is angled approximately 60+/−2 degrees with respect to the longitudinal axis of the handle in an opposite angle from the first part of the first paddle; and
   wherein the handle axis is disposed between the first paddle axis and the second paddle axis.

21. The retraction device of 20, wherein the first part of the first paddle is curved about a curved second curvature axis parallel to and radially within the curve of the first part of the first paddle about the first curvature axis.

\* \* \* \* \*